United States Patent [19]

Cliffe et al.

[11] Patent Number: 5,430,033
[45] Date of Patent: Jul. 4, 1995

[54] PIPERAZINE DERIVATIVES

[75] Inventors: Ian A. Cliffe, Farnham Common; Anderson D. Ifill, Didcot; Howard L. Mansell, Burnham; Terence J. Ward, Reading; Alan C. White, Englefield Green, all of England

[73] Assignee: John Wyeth & Brother Ltd., Maidenhead, England

[21] Appl. No.: 234,036

[22] Filed: Apr. 22, 1994

[30] Foreign Application Priority Data

Apr. 27, 1993 [GB] United Kingdom ............... 9308725

[51] Int. Cl.$^6$ ............... A61K 31/495; C07D 403/00; C07D 401/00; C07D 405/00
[52] U.S. Cl. ............... 514/254; 514/252; 544/295; 544/363; 544/364; 544/372; 544/373; 544/376; 544/377; 544/392
[58] Field of Search ............... 544/392, 295, 372, 363, 544/373, 364, 295, , 376, 377, 392; 514/252, 254

[56] References Cited

U.S. PATENT DOCUMENTS

| | | | |
|---|---|---|---|
| 3,732,229 | 5/1973 | Bysouth | 260/268 |
| 3,947,411 | 3/1976 | Vigelius et al. | 544/392 |
| 4,613,598 | 9/1986 | Fukami et al. | 544/392 |
| 4,845,221 | 7/1989 | Stack et al. | 544/392 |
| 5,053,409 | 10/1991 | Okushima et al. | 544/392 |

FOREIGN PATENT DOCUMENTS

| | | |
|---|---|---|
| 574313 | 12/1993 | European Pat. Off. . |
| 1171251 | 11/1969 | United Kingdom . |

OTHER PUBLICATIONS

Peglion et al, Chem. Abst. 120(19):245155d (1993) Abstract of EP 574313 (Dec. 15, 1993).
Reitz, Chem. Abst. 119(11):117276m (1993) Abstract of WO 93/04682 (Mar. 18, 1993).
Reitz, Chem Abst. 119(9):95555x (1993) Abstract of WO 93/04683, (Mar. 18, 1993).
Zhang et al., Yaoxue Xuebao, 21(5), 345–55, CA106(15): 119384a) (1986).
R. A. Magarian and W. L. Nobles, J. Pharm. Sci., 56(8), 987–992 (1967).

*Primary Examiner*—Cecilia Tsang
*Attorney, Agent, or Firm*—R. F. Boswell, Jr.

[57] ABSTRACT

Piperazine derivatives of formula I

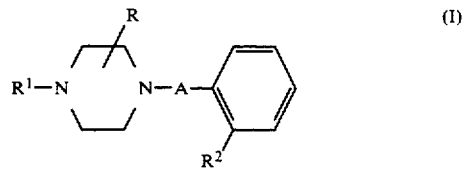

and their pharmaceutically acceptable acid addition salts are 5-HT$_{1A}$ binding agents, particularly 5-HT$_{1A}$ antagonists and may be used, for example, as anxiolytics. In the formula R is hydrogen or one or two lower alkyl groups, R$^1$ is a mono of bicyclic aryl or heteroaryl radical, R$^2$ is aryl and A is a C$_{2-5}$ alkylene chain optionally substituted by lower alkyl.

7 Claims, No Drawings

PIPERAZINE DERIVATIVES

This invention relates to piperazine derivatives, to processes for their preparation, to their use and to pharmaceutical compositions containing them. The novel compounds act upon the central nervous system by binding to 5-HT receptors (as more fully explained below) and hence can be used as medicaments for treating human and other mammals.

The novel compounds of the invention are those of the general formula

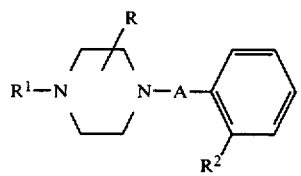

(I)

and the pharmaceutically acceptable acid addition salts thereof.

In formula (I):

R represents-hydrogen or one or two same or different (lower)alkyl groups, $R^1$ is a mono- or bicyclic aryl or heteroaryl radical, $R^2$ is an aryl radical and A is an alkylene chain of 2 to 5 carbon atoms optionally substituted by one or more lower alkyl groups.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert.-butyl, pentyl and isopentyl. A cycloalkyl group preferably contains 3 to 7 carbon atoms.

When used herein "aryl" means an aromatic radical having 6 to 10 carbon atoms (eg phenyl or naphthyl) which optionally may be substituted by one or more substituents. Preferred substituents are lower alkyl, hydroxy, lower alkoxy (eg methoxy, ethoxy, propoxy, butoxy), halogen, hydroxy(lower)alkyl, (lower)alkoxy(lower)alkyl, (lower)alkoyloxy(lower)alkyl, (lower)alkylcarbonyl, (lower)alkylcarbonyl(lower)alkyl, halo(lower)alkyl (eg trifluoromethyl), nitro, nitrile, aminocarbonyl, (lower)alkoxycarbonyl, amino, (lower)alkylamino, di(lower)alkylamino, (lower)alkoxycarbonyloxyalkyl, aminocarbonyloxy(lower)alkyl, (lower)alkylaminocarbonyloxy(lower)alkyl, di(lower)alkylaminocarbonyloxy(lower)alkyl, (lower)alkoxycarbonyl(lower)alkyl, aminocarbonyl(lower)alkyl, (lower)alkylaminocarbonyl(lower)alkyl, di(lower)alkylaminocarbonyl(lower)alkyl, acylamino, arylcarbonyl, arylcarbonyl(lower)alkyl and formyl. Two substituents on the aromatic ring may be connected together to form another ring system. For example $R^1$ may be a bicyclic oxygen-containing radical of the formula

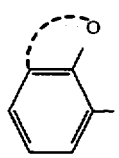

wherein the heterocyclic ring containing the oxygen atom contains a total of 5 to 7 ring members, said heterocyclic ring being non-aromatic and optionally containing one or more hetero ring members (eg O, N or S) in addition to the oxygen atom illustrated and the bicyclic oxygen radical being optionally substituted by one or more substituents such as the substituents mentioned above in connection with "aryl". A preferred example of such a bicyclic oxygen radical is an optionally substituted radical of the formula

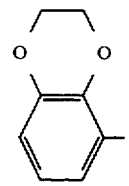

Preferably $R^1$ is a phenyl radical containing a substituent in the ortho position. A particularly preferred example of $R^1$ is o-(lower)alkoxyphenyl eg o-methoxyphenyl. A preferred example of $R^2$ is phenyl or phenyl monosubstituted by one of the preferred substituents given above.

The term "heteroaryl" refers to an aromatic radical containing one or more hetero ring atoms (eg oxygen, nitrogen, sulphur) and which may be optionally substituted by one or more substituents. Examples of suitable substituents are given above in connection with "aryl" radicals. The heteroaryl radical may, for example, be a bicyclic radical containing 8 to 11 ring atoms or a monocyclic radical containing 5 to 7 ring atoms. Preferably the hetero ring contains a nitrogen hetero atom with or without one or more further hetero atoms. When $R^1$ is a heteroaryl group it is preferably an optionally substituted pyrimidyl, quinolinyl, isoquinolinyl, or indolyl radical. Examples of substituents are given above in connection with the "aryl" radical.

Examples of the alkylene chain A include —CH$_2$CH$_2$—, —CH$_2$CH$_2$CH$_2$—, —CH$_2$CH(CH$_3$)— and —CH$_2$CH$_2$CH(CH$_3$)—.

Preferred compounds have the following substituents either independently or in combination:

(a) R is hydrogen (b) $R^1$ is aryl, for example o-(lower)alkoxyphenyl (eg o-methoxyphenyl)

(c) $R^2$ is phenyl (d) A is —CH$_2$CH$_2$—

The compounds of the invention may be prepared by methods known in the art from known starting materials or starting materials that may be prepared by conventional methods.

One method of preparing the compounds of the invention comprises alkylation of a piperazine of formula (II)

$R^1$—N⟨   ⟩NH
      (with R above)

(where R and $R^1$ are as defined above) with an alkylating agent providing the group

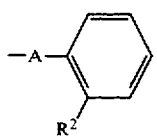

(where A and $R^2$ are as defined above). The alkylating agent may be, for example a compound of formula

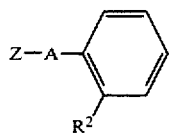

where A and $R^2$ are as defined above and Z is a leaving group such as halogen or an alkyl- or aryl-sulphonyloxy group. Alternatively the alkylation may be carded out by acylating the piperazine of formula (II) with an acid of formula

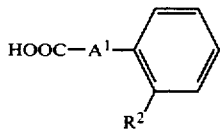

(where $R^2$ is as defined above and $A^1$ is an alkylene chain of 1 to 4 carbon atoms optionally substituted by one or more lower alkyl groups) or with an acylating derivative thereof to give an intermediate amide of formula

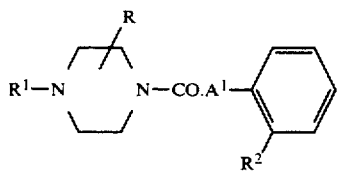

and reducing the amide. Examples of acylating derivatives include the acid halides (eg acid chlorides) azides, anhydrides, irnidazolides (eg obtained from carbonyldiimidazole), activated esters or O-acyl ureas obtained from a carbodiimide such as a dialkylcarbodiimide particularly dicyclohexyl-carbodiimide. Preferably the piperazine is acylated with a coupling agent such as 1,1'-carbonyldiimidazole, isobutylchloroformate or diphenylphosphinyl chloride. The reduction of the amide may be carried out with a hydride reducing agent (eg borane-dimethylsulphide).

In an alternative method of preparation a compound of formula

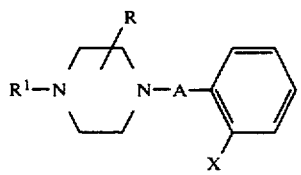

where R, $R^1$ and A are as defined above and X is halogen (preferably bromine) is arylated with an arylating reagent containing the group $R^2$. The reaction can be carried out by methods known for the preparation of bi-aryl groups. See, for example, Comprehensive Organic Synthesis, edited by B M Frost and I Fleming, Vol 3, Chapter 2.3, Pergamon Press, 1991. In a preferred method the compound of (VII) is subjected to a transition metal (eg palladium) catalysed cross coupling reaction. For example the compound of formula (VII) in presence of base and a palladium catalyst, eg tetrakis (triphenylphoshine)palladium (o), is reacted with an arylboronic acid, arylboronate, arylzinc chloride, arylstannane, or an arylmagnesium bromide.

The starting halo compound of formula (VII) may be prepared by reacting a piperazine of formula (II) with an acid of formula (V) where $R^2$ is halogen and reducing the intermediate amide by a process analogous to that described above.

If in any of the other processes mentioned herein, a substituent on the group $R^1$ is other than the one required the substituent may be converted to the desired substituent by known methods.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention may contain one or more asymmetric carbon atoms, in which case the compounds can exist in different steroisomeric forms. The compounds can be for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors. In pharmacological testing it has been shown that the compounds particularly bind to receptors of the 5-$HT_{1A}$ type. In general, the compounds selectively bind to receptors of the 5-$HT_{1A}$ type to a much greater extent than they bind to other receptors such as $\alpha_1$ and $D_2$ receptors and exhibit activity as 5-$HT_{1A}$ antagonists in pharmacological testing. The compounds of the invention can be used for the treatment of CNS disorders, such as schizophrenia and anxiety (eg generalised anxiety disorders, panic attacks and obsessive compuslive disorders) in mammals, particularly humans. They may also be used as antidepressants, hypotensives and as agents for regulating the sleep/wake cycle, feeding behaviour and/or sexual function and as cognition enhancing agents.

The compounds of the invention are tested for 5-$HT_{1A}$ receptor binding activity in rat hippocampal membrane homogenate by the method of B S Alexander and M D Wood, J Pharm Pharmacol, 1988, 40, 888-891. The compound of Example 3 below, a representative compound of the invention, had an $IC_{50}$ of 2 nM.

The compounds are tested for 5-$HT_{1A}$ receptor antagonism activity in a test involving the antagonism of 5-carboxamidotryptamine in the guinea-pig ileum in vitro (based upon the procedure of Fozard et al, Br J Pharmac, 1985, 86, 601P). The compound of Example 3 had a $pA_2$ of 8.1.

The invention also provides a pharmaceutical composition comprising a compound of formula I or a pharmaceutically acceptable acid addition salt thereof in association with a pharmaceutically acceptable carder. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carder is a finely divided solid which is in admixture with the finely divided active ingredient.

In tablets the active ingredient is mixed with a carrier having the necessary compression properties in suitable proportions and compacted in the shape and size desired. The powders and tablets preferably contain up to 99%, e.g. from 0.03 to 99%. preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution, alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compostions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

1-(2-(2-Bromophenyl)acetyl)-4-(2-methoxyphenyl)piperazine

A stirred solution of 2-bromophenylacetic acid (28.4 g, 132 mmol) in chloroform (200 ml) was treated dropwise over 10 rain with 1,1'-carbonyldiimidazole (21.4 g, 132 mmol) in chloroform (120 ml) under argon, after 1 h treated with 2-(methoxyphenyl)piperazine (24.4 g, 127 mmol) in chloroform (100 ml), after 18 h washed with 0.5 N-HCl (2×200 ml), 0.5 N-NaOH (2×200 ml), and brine (200 ml), dried ($MgSO_4$), and evaporated in vacuo. The oil was crystallised by trituration with cyclohexane (100 ml) to give the product (27.0 g), m.p. 95°–97°.

(Found: C, 58.7; H, 5.5; N, 7.35. $C_{19}H_{21}BrN_2O_2$ requires C, 58.6; H, 5.4; N, 7.2%).

EXAMPLE 2

1-(2-(2-Bromophenyl)ethyl)-4-(2-methoxyphenyl)piperazine

A stirred solution of the product of Example 1 (25.7 g, 66.1 mmol) in dry tetrahydrofuran (THF, 100 ml) was heated under reflux under an atomosphere of argon, treated dropwise over 25 min with borane-dimethylsulphide (12.5 ml, 131.7 mmol) in THF (100 ml), after 90 min cooled to room temperature, and the suspension treated dropwise with methanol (100 ml), followed by concentrated hydrochloric acid (50 ml). The solution was stirred for 1 h and the precipitate filtered and washed with acetonitrile (20 ml) and ether (3×20 ml) to give the product (15.7 g) m.p. 190°–195°.

Found: C, 50.4; H, 6.0; N, 6.2. $C_{19}H_{23}BrN_2O.2HCl$ $\frac{1}{4}H_2O$ requires C, 50.4; H, 5.7; N, 6.2%).

EXAMPLE 3

1-(2-(2-biphenyl)ethyl)-4-(2-methoxyphenyl)piperazine

2M-Sodium carbonate (10 ml) was added to a solution of phenylboronic acid (0.72 g, 5.9 mmol) dissolved in the minimum volume of ethanol. The aqueous solution was added to a stirred suspension of the dihydrochloride salt of the product of Example 2 (2.00 g, 5.3 mmol) and crude tetrakis (triphenylphosphine) palladium (o) as catalyst (0.50 g, 10 mol in toluene (55 ml). The reaction mixture was heated under reflux for 2.5 h, a further quantity of crude catalyst (0.20 g) added and heating under reflux continued for 5.5 h. A further quantity of crude catalyst (0.20 g) added and heating under reflux continued for 5.5 h. A further sample of phenylboronic acid (0.72 g) and pure catalyst (0.31 g) were added and heating continued for a further 6 h. The cooled reaction mixture was filtered and brine (40 ml) added to the tiltrate. The organic phase was washed with brine (40 ml), water (40 ml), dried (MgSO4), concentrated, and chromatographed [silica; ethyl acetateohexane (1:1 to 2:1 )] to afford a brown oil, which solidified on standing. The solid was dissolved in acetonitrile and acidified with etheral hydrogen chloride to afford the dihydrochloride salt of the product as off white crystals (0.92 g), m.p. 215.5°–218.5° C.

Found: C,67.0; H, 6.8; N, 6.5. $C_{25}H_{28}N_2O.2HCl$ requires C, 67.4; H, 6.8; N, 6.3.

We claim:

1. A compound of formula (I)

and the pharmaceutically acceptable acid addition salts thereof, wherein

R represents hydrogen or one or two same or different $C_1$-$C_6$ alkyl groups, $R^1$ is a mono- or bicyclic aryl radical selected from phenyl, naphthyl; a monocyclic heteroaryl group of 5 or 6 ring atoms one or two of which are nitrogen; or a bicyclic heteroaryl radical of 9 or 10 ring atoms, one or two of which are nitrogen atoms wherein the nitrogen atoms are not common to the two flags, wherein the aryl or heteroaryl group may be optionally substituted by one or more substituents selected from $C_1$-$C_6$ alkyl, hydroxy, $C_1$-$C_6$-alkoxy, halogen, hydroxy-$C_1$-$C_6$-alkyl, $C_1$-$C_6$-alkoxy-$C_1$-$C_6$-alkyl, $C_1$-$C_6$-alkoyloxy-$C_1$-$C_6$-alkyl, $C_1$-$C_6$-alkylcarbonyl, $C_1$-$C_6$-alkylcarbonyl-$C_1$-$C_6$-alkyl, halo-$C_1$-$C_6$-alkyl, nitro, nitrilo, aminocarbonyl, $C_1$-$C_6$-alkoxycarbonyl, amino, $C_1$-$C_6$-alkylamino, di-$C_1$-$C_6$-alkylamino, $C_1$-$C_6$-alkoxycarbonyloxy-$C_1$-$C_6$-alkyl, aminocarbonyloxy-$C_1$-$C_6$-alkyl, $C_1$-$C_6$-alkylaminocarbonyloxy-$C_1$-$C_6$-alkyl, di-$C_1$-$C_6$-alkylaminocarbonyloxy-$C_1$-$C_6$-alkyl, $C_1$-$C_6$-alkoxycarbonyl-$C_1$-$C_6$-alkyl, aminocarbonyl-$C_1$-$C_6$-alkyl, $C_1$-$C_6$-alkylaminocarbonyl-$C_1$-$C_6$-alkyl, di-$C_1$-$C_6$-alkylaminocarbonyl-$C_1$-$C_6$-alkyl, $C_1$-$C_6$-acylamino, phenyl- or naphthylcaxbonyl, phenyl- or naphthylcarbonyl-$C_1$-$C_6$-alkyl and formyl- or $R^1$ is an aryl group of the formula wherein the heterocyclic ting containing the oxygen atom is non-aromatic, contains a total of 5 to 7 ring members, and optionally contains one or two further heteroatom ring members selected from oxygen and sulfur in addition to the oxygen atom, and said non-aromatic heterocyelic ring may be optionally substituted by one or more substituents as enumerated above as optional substituents for the aryl or heretoaryl group; $R^2$ is phenyl or naphthyl optionally substituted as above for an aryl or heteroaryl radical, and A is an alkylene chain of 2 to 5 carbon atoms optionally substituted by one or more $C_1$-$C_6$-alkyl groups.

2. A compound as claimed in claim 1 wherein R is hydrogen.

3. A compound as claimed in claim 1 wherein $R^1$ is o-$C_1$-$C_6$-alkoxyphenyl.

4. A compound as claimed in claim 1 wherein $R^2$ is phenyl.

5. A compound as claimed in claim 1 wherein A is —$CH_2$—$CH_2$—.

6. A compound as claimed in claim 1 which is 1-(2-2-biphenyl)ethyl)-4-(2methoxyphenyl)piperazine or a pharmaceutically acceptable acid addition salt thereof.

7. A method for treating anxiety in a mammal which comprises administering to said mammal an effective amount of a compound claimed in claim 1.

* * * * *